US006420546B1

(12) United States Patent
Seliger et al.

(10) Patent No.: US 6,420,546 B1
(45) Date of Patent: *Jul. 16, 2002

(54) OLIGORIBONUCLEOTIDE AND RIBOZYME ANALOGS WITH TERMINAL 3'—3' AND/OR 5'—5' LINKAGES

(75) Inventors: Heinz Hartmut Seliger, Elchingen; Flavio Ramalho Ortigao, Ulm; Hannelore Rösch; Rudi Rösch, both of Erbach; Bernd Krist, Ulm, all of (DE)

(73) Assignee: Aventis Pharma Deutschland GmbH, Frankfurt am Main (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/059,331

(22) Filed: Apr. 14, 1998

Related U.S. Application Data (63) Continuation of application No. 08/562,635, filed on Nov. 27, 1995, now abandoned, which is a continuation of application No. 08/126,228, filed on Sep. 23, 1993, now abandoned.

(30) Foreign Application Priority Data

Sep. 24, 1992 (DE) .......................................... 42 31 949

(51) Int. Cl.$^7$ .................... C07H 21/02; C07H 21/04; C12Q 1/68; A01N 43/04

(52) U.S. Cl. ..................... 536/24.1; 536/23.1; 536/24.5; 536/25.1; 536/25.3; 536/26.13; 536/26.71; 435/6; 514/44

(58) Field of Search ............................. 536/23.1, 24.1, 536/24.5, 25.1, 25.3, 26.13, 26.71; 435/6; 514/44

(56) References Cited

U.S. PATENT DOCUMENTS 5,399,676 A * 3/1995 Froehler et al. ........... 536/23.1

FOREIGN PATENT DOCUMENTS

| CA | 2017369 | 11/1990 |
| EP | 0 464 638 A2 | 1/1992 |
| EP | 0 552 766 A2 | 7/1993 |
| EP | 0 552 767 A2 | 7/1993 |
| WO | WO 92/13869 | 8/1992 |

OTHER PUBLICATIONS

Koga et al. "Alternating–oligothymidylates with alternating (3'–3')–and 5'–5')–internucleotidic phosphodiester linkages as models for antisense oligodeoxyribonucleotides" J. Org. Chem. vol. 56, pp. 3757–3759, Jun. 1991.*

S. Agrawal, "Antisense oligonucleotides as antiviral agents," *Trends In Biotechnology* 10(5):152–158 (1992).

Atkinson et al., "Solid–phase Synthesis of Oligodeoxyribonucleotides by the Phosphite–triester Method," *Oligonucleotide Synthesis*, pp. 35–49 (1984).

Benseler et al., "Synthesis of Suitably–Protected Phosphoramidites of 2'–Fluoro–2'–Deoxyguanosine and 2'–Amino–2'–Deoxyguanosine for Incorporation into Oligoribonucleotides," *Nucleosides & Nucleotides* 11:1333–1351 (1992).

(List continued on next page.)

Primary Examiner—Jezia Riley
(74) Attorney, Agent, or Firm—Finnegan, Henderson, Farabow, Garrett and Dunner, L.L.P.

(57) ABSTRACT

The invention relates to oligoribonucleotide analogs with terminal 3'—3' and/or 5'—5' internucleotide linkages. This modification stabilizes the molecules altered in this way, including ribozymes, without adversely altering their properties, including, where appropriate, catalytic activities.

10 Claims, 4 Drawing Sheets

OTHER PUBLICATIONS

Beaucage et al., "Advances in the Synthesis of Oligonucleotides by the Phosphoramidite Approach," *Tetrahedron* 48(12):2223–2311 (1992).

Branch et al., "Efficient trans cleavage and a common structural motif for the ribozymes of the human hepatitis δ agent," *Proc. Natl. Acad. Sci. USA* 88:10163–10167 (1991).

Castanotto et al., "Biological and Functional Aspects of Catalytic RNAs," *Critical Reviews in Eukaryotic Gene Expression* 2(4):331–357 (1992).

T.R. Cech, "Ribozymes and Their Medical Implications," *J. Am. Med. Assn.* 260(20):3030–3034 (1988).

Christoffersen and Marr, "Ribozymes as Human Therapeutic Agents," *J. Med. Chem.* 38(12):2023–2037 (1995).

Chubb and Hogan, "Human therapeutics based on triple helix technology," *TIBTECH* 10:132–136 (1992).

Curiel et al., "Adenovirus enhancement of transferrin–polylysine–mediated gene delivery," *Proc. Natl. Acad. Sci. USA* 88:8850–8854 (1991).

Forster and Altman, "External Guide Sequences for an RNA Enzyme," *Science* 249:783–786 (1990).

Gao et al., "Direct In Vivo Gene Transfer to Airway Epithelium Employing Adenovirus–Polylysine–DNA Complexes," *Human Gene Therapy* 4:17–24 (1993).

J. Goodchild, "Conjugates of Oligonucleotides and Modified Oligonucleotides: A Review of Their Synthesis and Properties," *Bioconjugate Chem.* 1(3):165–187 (1990).

Hampel et al., "'Hairpin' catalytic RNA model: evidence for helices and sequence requirement for substrate RNA," *Nucl. Acids Res.* 18(2):299–304 (1990).

Haseloff and Gerlach, "Simple RNA enzymes with new and highly specific endoribonuclease activities," *Nature* 334:585–591 (1988).

Héléne and Toulmé, "Specific regulation of gene expression by antisense, sense and antigene nucleic acids," *Biochimica et Biophysica Acta* 1049:99–125 (1990).

Iribarren et al., "2'–O–Alkyl oligoribonucleotides as antisense probes", *Proc. Natl. Acad. Sci. USA* 87:7747–7751 (1990).

Kashani–Sabet et al., "Reversal of the Malignant Phenotype by an Anti–ras Ribozyme," *Antisense Research & Development* 2:3–15 (1992).

Lyttle et al., "Nucleoside Phosphoramidites and Coupling Protocols for Solid–Phase RNA Synthesis," *J. Org. Chem.* 56:4608–4615 (1991).

MacKellar et al., "Synthesis and physical properties of anti–HIV antisense oligonucleotides bearing terminal lipophilic groups," *Nucl. Acids Res.* 20(13):3411–3417 (1992).

J. Joseph Marr, "Ribozymes as therapeutic agents," *Drug Discovery Today* 1(3):94–102 (1996).

Matteucci and Caruthers, "The Use of Zinc Bromide for Removal of Dimethoxytrityl Ethers from Deoxynucleosides," *Tetrahedron Letters* 21:3243–3246 (1980).

Mergny et al., "Triple Helix–Specific Ligands," *Science* 256:1681–1684 (1992).

Oberhauser and Wagner, "Effective incorporation of 2'–O–methyl–oligoribonucleotides into liposomes and enhanced cell association through modification with thio-cholesterol," *Nucl. Acids Res.* 20(3):533–538 (1992).

Olsen et al., "Study of a Hammerhead Ribozyme Containing 2'–Modified Adenosine Residues," *Biochemistry* 30:9735–9741 (1991).

Pieken et al., "Kinetic Characterization of Ribonuclease–Resistant 2'–Modified Hammerhead Ribozymes," *Science* 253:314–317 (1991).

Renneisen et al., "Inhibition of Expression of Human Immunodeficiency Virus–1 in Vitro by Antibody–targeted Liposomes Containing Antisense RNA to the env Region," *J. Biol. Chem.* 256(27):16337–16342 (1990).

San et al., "Safety and Short–Term Toxicity of a Novel Cationic Lipid Formulation for Human Gene Therapy," *Human Gene Therapy* 4:781–788 (1993).

Sarver et al., "Ribozymes as Potential Anti–HIV–1 Therapeutic Agents," *Science* 247:1222–1225 (1990).

Scanlon et al., "Ribozyme–mediated cleavage of c–fos mRNA reduced gene expression of DNA synthesis enzymes and metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl. Acids Res.* 18(18):5433–5441 (1990).

Seliger et al., "Oligonucleotide Analogues with Terminal 3'–3'–And 5'–5'–Internucleotidic Linkages as Antisense Inhibitors of Viral Gene Expression," *Nucleosides & Nucleotides* 10(1–3):469–477 (1991).

Sproat and Lamond, "2'–O–Methyloligoribonucleotides: synthesis and applications," *Oligonucleotides and Analogues*, pp. 49–87 (1991).

Stein and Cheng, "Antisense Oligonucleotides as Therapeutic Agents—Is the Bullet Really Magical?," *Science* 261:1004–1012 (1993).

Stull and Szoka, "Antigene, Ribozyme and Aptamer Nucleic Acid Drugs: Progress and Prospects," *Pharmaceutical Research* 12(4):465–483 (1995).

C.H. Suelter, "A Practical Guide Enzymology," pp. 231–254 (1985).

Olke Uhlenbeck, "A small catalytic oligoribonucleotide," *Nature* 328:596–600 (1987).

Uhlmann and Peyman, "Antisense Oligonucleotides: A New Therapeutic Principle," *Chemical Reviews* 90(4):543–583 (1990).

Whitesell et al., "In Vivo Modulation of N–myc Expression by Continuous Perfusion with an Antisense Oligonucleotide," *Antisense Research and Development* 1:343–350 (1991).

Williams et al., "Function of specific 2'–hydroxyl groups of guanosines in a hammerhead ribozyme probed by 2' modifications," *Proc. Natl. Acad. Sci. USA* 89:918–921 (1992).

Ortigao et al., "Antisense Effect of Oligodeoxynucleotides with Inverted Terminal Internucleotideic Linkages . . .", Antisense Research and Development, vol. 2, pp. 129–146 (1992).*

Beigelman et al, "Chemical Modification of Hammerhead Ribozymes", The Journal of Biological Chemistry vol. 270, pp. 25702–2570 (1995).*

* cited by examiner

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
       (A) LENGTH: 35 base pairs
       (B) TYPE: nucleic acid
       (C) STRANDEDNESS: single
       (D) TOPOLOGY: linear (ii) MOLECULE TYPE: Other
       (A) DESCRIPTION: Ribonucleotide (vi) ORIGINAL SOURCE:
       (B) STRAIN: "hammerhead" ribozyme (ix) FEATURE:
       (A) NAME/KEY: misc_feature
       (B) LOCATION: 35
       (D) OTHER INFORMATION: /note= "Inverted structure at 3'
           terminus with or without 2'-fluoro-2-desoxynucleosides"

(xi) SEQUENCE DESCRIPTION: SEQ ID NO: 1:

AAAGAUCUGA UGAGGCCGUU AGGCCGAAAC AGGGA                               35

(2) INFORMATION FOR SEQ ID NO: 2:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: Other
       (A) DESCRIPTION: Ribonucleotide (vi) ORIGINAL SOURCE:
       (B) STRAIN: "hammerhead" ribozyme (xi) SEQUENCE DESCRIPTION: SEQ ID NO: 2:

GCCCCUGUCA UCUUUUGUCC                                                20

(2) INFORMATION FOR SEQ ID NO: 3:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (ii) MOLECULE TYPE: Other
       (A) DESCRIPTION: Ribonucleotide

```
        (vi) ORIGINAL SOURCE:
             (B) STRAIN: "hammerhead" ribozyme (xi) SEQUENCE DESCRIPTION: SEQ ID NO: 3:

AAGAUCUGAU GAGGCCGUUA GGCCGAAACA GGGA                              34

(2) INFORMATION FOR SEQ ID NO: 4:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (ii) MOLECULE TYPE: Other
         (A) DESCRIPTION: Ribonucleotide

(vi) ORIGINAL SOURCE:
         (B) STRAIN: "hammerhead" ribozyme (xi) SEQUENCE DESCRIPTION: SEQ ID NO: 4:

AAAGAUCUGA UGAGGCCGUU AGGCCGAAAC AGGG                              34
```

OLIGORIBONUCLEOTIDE AND RIBOZYME ANALOGS WITH TERMINAL 3'—3' AND/OR 5'—5' LINKAGES

This application is a continuation of U.S. application Ser. No. 08/562,635, filed Nov. 27, 1995, now abandoned, which is a continuation of U.S. application Ser. No. 08/126,228, filed Sep. 23, 1993, now abandoned, both of which are incorporated herein by reference.

The invention relates to oligoribonucleotide analogs with terminal 3'—3' and/or 5'—5' internucleotide linkages. This modification stabilizes the molecules altered in this way, including ribozymes, without adversely altering their properties, including, where appropriate, catalytic activities.

Nucleic acid fragments whose sequence is complementary to the coding or sense sequence of a messenger RNA or to the codogenic strand of the DNA are called antisense oligonucleotides. Oligonucleotides of this type are increasingly being used for inhibiting gene expression, usually from the viewpoint of medical therapy, in vitro, in cell culture systems and in vivo (1. E. Uhlmann, A. Peyman, Chem. Rev. 90 (1990) 543–584; 2. J. Goodchild, Bioconjugate Chem. 1 (1990) 165–187; 3. L. Whitesell, A. Rosolen, L. Neckers, Antisense Research and Development 1 (1991) 343).

Variations of the antisense principle are:
I. Triple helix-forming oligonucleotides: nucleic acid fragments which are able to bind to the DNA double strand to form a triple helix and which modulate gene expression by inhibiting transcription (J. Chubb and M. Hogan, TIBTECE 10 (1992) 132–136).
II. Ribozymes: Ribonucleic acid fragments with enzymatic activity which comprises cleavage of the target RNA, for example an zRNA, after the specific binding of the ribozyme by the same (T. R. Cech, J. Am. Med. Assoc. 260 (1988) 3030).

For it to be possible to employ antisense oligonucleotides, triple helix-forming oligonucleotides and ribozymes in biological systems it is, however, necessary for the following conditions to be fulfilled (E. Uhlmann, A. Peyman, Chem. Rev. 90 (1990) 543–584):
1. on the one hand they must be readily soluble in water, but on the other hand easily pass through the lipophilic cell membrane,
2. they must be sufficiently stable to degradation inside the cell, i.e. stable to nucleases,
3. they must form stable hybrids with in intracellular nucleic acids at physiological temperatures,
4. the hybridization must be selective; the difference in the dissociation temperature to an oligonucleotide which results in a mispairing must be sufficiently large for it still to be possible for the latter to be specifically washed out,
5. in the case of ribozymes, the catalytic activity must be retained.

Unmodified oligonucleotides and, in particular, unmodified oligoribonucleotides are subject to extensive nucleolytic degradation. This is why at an early stage investigations were carried out into the structural modification of oligonucleotides so that they better meet the abovementioned requirements, in particular are better protected against nuclease degradation. For this purpose a large number of oligonucleotide analogs has been prepared, in some cases with enormous synthetic effort (1. E. Uhlmann, A. Peyman, Chem. Rev. 90 (1990) 543–584; 2. J. Goodchild, Bioconjugate Chem. 1 (1990) 165–187).

It was recently shown that 3'-3'- and/or 5'-51-terminally linked oligodeoxynucleotides and their analogs have distinctly increased stability against nucleolytic degradation (1. B. Seeliger, A. Fröhlich, M. Montenarh: Nucleosides+ Nucleotides 10 (1991) 469–477; Z. H. Rösch, A. Fröhlich, J. Ramalho-Ortigao, J. Flavio, M. Montenarh, H. Seeliger: EP 0464638A2). Surprisingly, it has now been found that the same type of terminal linkage, which is easily accessible synthetically a) is also able to stabilize the very much more labile oligoribonucleotides to nucleases,
b) is able to stabilize ribozymes (oligoribonucleotides with particular sequence requirements) to nucleases without impairing the catalytic activity,
c) is additionally able to stabilize oligoribonucleotides and ribozymes which have been protected from nucleases by chemical modification.

The invention therefore relates to oligoribonucleotides of the formula I in which
$R^1$ is hydrogen or a radical of the formula II $R^2$ is hydrogen or a radical of the formula III but where at least one of the radicals $R^2$ or $R^2$ is a radical of the formula II or III;
B is a base such as, for example, natural bases such as adenine, thymine, cytosine, guanine or unnatural bases such as, for example, purine, 2,6-diaminopurine, 7-deazaadenine, 7-deazaguanine, $N^4,N^4$-ethanocytosine or their prodrug forms;

$R^3$ is, independently of one another, OH, hydrogen, $O(C_1-C_{18})$alkyl, $O(C_2-C_{18})$alkenyl, F, $NH_2$ or its prodrug forms and $N_3$, but at least one $R^3$ radical is different from H, and $R^1$ is preferably OH, hydrogen, $O(C_1-C_6)$ alkyl, $O(C_2-C_6)$alkenyl, F, $NH_{23}$.

W and W' are, independently of one another, oxygen or sulfur;

Z and Z' are, independently of one another, $O^-$; $S^-$; $C_1-C_{18}$,-alkoxy, preferably $C_{12}-C_8$-alkoxy, particularly preferably $C_1-C_3$-alkoxy, especially methoxy; $C_1-C_{18}$-alkyl, preferably $C_1-C_8$-alkyl, particularly preferably $C_1-C_3$-alkyl, especially methyl; $NER^4$ with $R^4$=preferably $C_1-C_{18}$-alkyl, particularly preferably $C_1-C_8$-alkyl, especially $C_1-C_4$-alkyl or $C_1-C_4$-alkoxy-$C_1-C_6$-alkyl, preferably methoxyethyl; $NR^4R^5$, in which $R^4$ is as defined above and $R^5$ is preferably $C_1-C_{18}$,-alkyl, particularly preferably $C_1-C_8$-alkyl, especially $C_1-C_4$-alkyl, or in which $R^4$ and $R^5$ are, together with the nitrogen atom carrying them, a 5-6-membered heterocyclic ring which may additionally contain another hetero atom from the series comprising O, S and N, such as, for example, morpholine;

where X is OH, H, F, Cl, Br, $NH_2$, $N_3$, O—C(O)—$(C_1-C_{18})$-alkyl, O—C(O)—$(C_2-C_{18})$-alkenyl, O—C(O)—$(C_2-C_{18})$alkynyl, O—C(O)—$(C_6-C_{18})$aryl, O—$(C_1-C_{18})$-alkyl, O—$(C_2-C_{18})$-alkenyl, O—$(C_2C_{18})$alkynyl, O—$(C_6-C_{18})$aryl, P(O)YY', where Y and Y' are defined as Z and Z'. $R^3$ and X in formula II can together'form a cyclic phosphoric diester.

X is preferably OR, H, F, particularly preferably OH, and n is an integer from 5–60, preferably 10–40 and especially preferably 15–25, and their physiologically tolerated salts.

Aryl is to be understood to mean in this connection, for example, phenyl, phenyl substituted (1–3 times) by $C_1-C_6$-alkyl, $C_1-C_6$-alkoxy and/or halogen.

The oligoribonucleotides of the formula I are preferred. Furthermore preferred are oligoribonucleotides of the formula I in which $R^2$ is a radical of the formula III and $R^1$ is hydrogen; $R^1$ or $R^2$ is a radical of the formulae II and III respectively; or $R^2$ is hydrogen and $R^1$ is a radical of the formula II, where either W or Z in the latter case is not oxygen.

Furthermore, particular mention may be made of oligoribonucleotides of the formula I in which W is oxygen, or Z and W are both oxygen.

Furthermore, particular mention may be made of oligoribonucleotides of the formula I whose base sequence $B^1, B^2$, . . . $B^n$ corresponds to the sequence requirements for ribozymes.

Emphasis should be placed in this connection on hammerhead ribozymes (for example Uhlenbeck, Nature 328 (1987) 596; Haseloff, Gerlach, Nature 334 (1988) 585), the hairpin ribozymes (for example Hampel et al., Nucl. Acids. Res. 18 (1990) 299), the human hepatitis α-virus ribozyme (for example Branch, Robertson, Proc. Natl. Acad. Sci. USA 88 (1991) 10163) and the external guide sequence for RNase P (for example Forster, Altman, Science 249 (1990) 783), but very especially the hammerhead ribozymes.

Very particularly preferred oligoribonucleotides of the formula I are those in which $R^2$ is a radical of the formula III and $R^1$ is hydrogen.

Furthermore, mention may be made of oligoribonucleotides of the formula I which are additionally substituted by groups which favor intracellular uptake, which act in vitro or in vivo as reporter groups, and/or groups which, on hybridization of the oligoribonucleotide onto biological DNA or RNA, interact with these DNA or RNA molecules with binding or cleavage.

Examples of groups which favor intracellular uptake are lipophilic radicals such as alkyl radicals, for example with up to 18 carbon atoms, or cholesteryl, or thiocholesteryl (E. Uhlmann, A. Peyman, Chem. Rev. 90 (1990) 543–584; J. Goodchild, Bioconjugate Chem. 1 (1990) 165–187; B. Oberhauser, E. Wagner, Nucl. Acids Res. 20 (1992) 533; C. MacKellar et al., Nucl. Acids. Res. 20 (1992) 3411) or conjugates which utilize natural carrier systems such as, for example, bile acids or peptides for the appropriate receptor (for example receptor-mediated endocytosis).

Examples of reporter groups are fluorescent groups (for example acridinyl, dansyl, fluoresceinyl) or chemiluminescent groups such as, for example, acridinium ester groups.

Examples of oligonucleotide conjugates which bind to and/or cleave nucleic acids are to be found in the following references. (E. Uhlmann, A. Peyman, Chem. Rev. 90 (1990) 543–584; J. Goodchild, Bioconjugate Chem. 1 (1990) 165–187; Helene, Toulme, Biochim. Biophys. Acta 1049 (1990) 99).

Conjugate partners are, inter alia, acridine, psoralen, chloroethylaminoaryl, phenanthridine, azidophenacyl, azidoproflavine, phenazine, phenanthroline/Cu, porphyrin/Fe, benzo[e] pyridoindole, EDTA/Fe (Mergny et al., Science 256 (1992) 1681).

The characteristic structural modification of the oligoribonucleotides according to the invention comprises the internucleotide linkages at both ends of the chain being altered, i.e. being 3'—3' or 5'—5' linkages in place of biological 3'-5' linkages. It has been found, surprisingly, that this minimal structural modification suffices to stabilize such compounds against nuclease degradation without adversely altering other properties, for example enzymatic activities.

As described hereinafter, the only slight structural modification results in a hybridization behavior which is almost identical to that of the biological oligoribonucleotides. This also results in the general applicability of these compounds as inhibitors of gene expression.

The compounds of the formula I are prepared in the same way as the synthesis of biological oligonucleotides in solution or, preferably, on a solid phase, where appropriate with the assistance of an automatic synthesizer. The invention therefore additionally relates to a process for the preparation of the oligoribonucleotides of the formula I, which comprises a) reacting a nucleotide unit with 3'- or 5'-terminal phosphorus(III) or phosphorus(V) groups or its activated derivative with another nucleotide unit with a 3'- or 5'-terminal free hydroxyl group, or b) assembling the oligonucleotide by fragments in the same way, eliminating where appropriate one or more protective groups temporarily introduced to protect other functionalities in the oligonucleotides obtained according to a) or b), and converting the oligonucleotides of the formula I obtained in this way where appropriate into their physiologically tolerated salt.

The starting component employed for the solid-phase synthesis for preparing oligoribonucleotides with terminally inverted 3'-3' linkage is a support resin to which the first nucleoside monomer is attached via the 5'-OH group. This component is prepared using a support resin prepared by methods known from the literature (T. Atkinson, M. Smith in Oligonucleotide Synthesis, M. J. Gait (ed), 35–49

(1984)), preferably silica gel or controlled pore glass which is functionalized with amino groups. It is reacted with a nucleoside derivative which is protected on the nucleoside base and on the 3'-OH group and which has previously been converted into the 5'-p-nitrophenylsuccinate. The base-protective groups preferably employed are acyl groups, for example benzoyl, isobutyryl or phenoxyacetyl. The 3' position is preferably protected by the dimethoxytrityl protective group, which can be introduced as described by M. D. Matteucci, M. H. Caruthers, Tetrahedron Letters 21 (1980), pages 3243–3246.

Further assembly of the oligoribonucleotide chain up to the penultimate chain member takes place by methods known from the literature (Beaucage, Iyer, Tetrahedron 48 (1992) 2223), preferably using nucleoside 3'-phosphorous ester amides or nucleoside 3'-H-phosphonates protected on the 5'-OH group by dimethoxytrityl groups. The 2'-hydroxyl group is preferably protected by the tert-butyldimethylsilyl group (M. Lyttle et al., J. Org. Chem. 56 (1991) 4608; Scaringe et al., Nucl. Acids Res. 18 (1990) 5433). The 2'-amino group (synthesis of compounds with $R^3=NH_2$) is preferably protected using the trifluoroacetyl group (Benseler et al., Nucleosides & Nucleotides 11 (1992) 1333). The last chain member employed is again a nucleoside 5'-phosphorous ester amide or a nucleoside H-phosphonate protected on the 3'-OH group, preferably using dimethoxytrityl. The preparation of an oligoribonucleotide chain of this type with terminally inverted internucleotide linkages is depicted diagrammatically hereinafter. (Phosphoramidite cycle for the preparation of oligonucleotides with 3'—3' and 5'—5' linkages at the ends.) Oligoribonucleotides with 3'—3' or 5'—5' linkages are prepared correspondingly.

Methods known from the literature are likewise used to incorporate 2'-modified ribonucleotide units such as, for example, 2'-O-alkyl 2'-deoxyribonucleotides (Iribarren et al., Proc. Natl. Acad. Sci. USA 87 (1990) 7747; Sproat, Lamond in Oligonucleotides and Analogues: F. Eckstein, Ed., IRL Press, Oxford 1991); 2'-F- and 2'-NH$_2$-2'-deoxyribonucleotides (Benseler et al., Nucleosides & Nucleotides 11 (1992) 1333; Pieken et al., Science 253 (1991) 314; Olsen et al., Biochemistry 30 (1991) 9735).

The oligoribonucleotides undergo terminal labeling for structure and sequence analyses, as described in Example 4 hereinafter. This takes place by radioactive labeling, preferably with the aid of 5'-$\gamma^{32}$P-ATP/polynucleotide kinase. This radioactive labeling takes place on the free 5'-OH group, i.e. at the opposite end of the nucleotide chain from an oligonucleotide with only biological 3'-5' linkages.

The sequences with 3'-3' inversion have a 5'-OH group at both ends and are therefore in some cases phosphorylated at both ends.

The oligonucleotides of the formula I are used for chemical hybridization methods which are based on addition onto double- or single-stranded nucleic acids or their cleavage for the regulation or suppression of the biological function of nucleic acids, and for the selective suppression of the expression of viral genome functions and for the prophylaxis and therapy of viral infections, for the suppression of oncogene function and for the therapy of cancers.

The behavior of an oligoribonucleotide of the formula I which has been assembled according to the invention and dissolved in blood serum can be regarded as a measure of the stability in vivo. The general test is described in Example 4. The oligoribonucleotides according to the invention are degraded much more slowly than the 3'–5' oligoribonucleotides.

Example 5 demonstrates that the oligoribonucleotides according to the invention which meet the sequence requirements for hammerhead ribozymes do not differ in their enzymatic activity from the unmodified ribozymes.

EXAMPLE 1

Synthesis of the 2'-fluoro-2-deoxynucleoside units (Annex 1)

5'-O-(Dimethoxytrityl)-2'-fluoro-2'-deoxyuridine 0.5 g (about 2 mmol) of 2'-fluoro-2'-deoxyuridine is coevaporated with 10 ml of abs. pyridine twice in a 50 ml Schlenk flask. The dried nucleoside is taken up in 25 ml of abs. pyridine and, at room temperature, 0.66 g (about 2.2 mmol) of dimethoxytrityl chloride and 10 mg of 4-dimethylaminopyridine are added. After three hours, 1 ml of methanol was added to the mixture, which was then evaporated to dryness in vacuo. The remaining oil is taken up in 50 ml of methylene chloride (deacidified over aluminum oxide) and extracted three times with 50 ml of water. The organic phase is dried over sodium sulfate. After the methylene chloride had been stripped off, the crude product remained as a solid foam. To remove more highly tritylated components and the tritanol, the crude product was digested with 30 ml of abs. benzene at 40–50° C.

0.75 g, corresponding to 67% of theory, of a white solid is obtained.

4-N-Acetyl-2'-fluoro-2'-deoxycytidine 1 g (about 4 mmol) of 2'-fluoro-2'-deoxycytidine hydrochloride is coevaporated with 20 ml of abs. pyridine twice and twice with 10 ml of abs. acetonitrile each time in a 100 ml Schlenk flask. The dried nucleosidic material is suspended in 40 ml of abs. DMF, and 0.6 ml (about 4.4 mmol) of acetic anhydride is added. Over the course of one day 0.5 ml (4.4 mmol) of abs. triethylamine is added dropwise to the mixture. The solvent is subsequently stripped off under oil pump vacuum. The crude product is washed with 50 ml of diethyl ether and subsequently dried. Purification was by column chromatography (silica gel 60 H, column 4×10 cm, mobile phase methylene chloride with 0.1% pyridine, gradient methanol); the product is eluted at 8% methanol.

On stripping off the solvent, 0.83 g (71% of the theoretical yield) of product remain.

5'-O-(Dimethoxytrityl)-4-N-acetyl-2'-fluoro-2'-deoxycytidine 4 mmol of 4-N-acetyl-2'-fluoro-2'-deoxycytidine are taken up in 25 ml of abs. pyridine in a 100 ml Schlenk flask and, at room temperature, 1.3 g (about 4.4 mmol) of dimethoxytrityl chloride and 20 mg of 4-dimethylaminopyridine are added. After three hours, 1 ml of methanol was added to the mixture, which was then evaporated to dryness in vacuo. The remaining oil is taken up in 50 ml of methylene chloride (deacidified over aluminum oxide) and extracted three times with 50 ml of water. The organic phase is dried over sodium sulfate. After the methylene chloride had been stripped off, the crude product remained as solid foam. The crude product is purified by chromatography on silica gel 60H (column 2×20 cm, mobile phase methylene chloride with 0.1% pyridine, gradient methanol). The product was eluted with 3% methanol in methylene chloride. After the solvent has been stripped off, 1.39 g (59% of theory) of a white foamy solid remain.

Phosphorous ester amides of 2'-fluoro-2'-deoxynucleosides 1 mmol of the protected monomer is dissolved in 5 ml of abs. methylene chloride and 1 ml of abs. diisopropylamine. A disposable syringe is used to add 1.2 mmol of chloro-N, N-diisopropylamino-β-cyanoethoxyphosphine dropwise under argon. After one hour, conversion is virtually quantitative, and the reaction can be stopped with 0.1 ml of methanol. The mixture is taken up in 20 ml of ethyl acetate and extracted three times with 20 ml of saturated NaCl solution each time. The organic phase is dried over sodium sulfate, and the solvent is stripped off. The crude product is taken up in 5 ml of methylene chloride and precipitated from 400 ml of abs. petroleum ether at room temperature. After the precipitate has been collected on a fritt, it is dried at the oil pump and stored at −20° C.

5'-O-(Dimethoxytrityl)-4-N-acetyl-2'-fluoro-2'-deoxycytidine-diisopropylamino-β-cyanoethoxyphosphine:

Batch: 0.59 g (1 mmol) of 5'-O-(dimethoxytrityl)-4-N-acetyl-2'-fluoro-2'-deoxycytidine Yield: 0.60 g (0.78 mmol, 78% of theory)

5'-(Dimethoxytrityl)-2'-fluoro-2'-deoxyuridine-diisopropylamino-β-cyanoethoxyphosphine:

Batch: 0.55 g (1 mmol) of 5'-O-(dimethoxytrityl)-2'-fluoro-2'-deoxyuridine

Yield: 0.61 g (0.83 mmol, 83% of theory)

EXAMPLE 2

Loading of CPG 10-1400-support material with 3'-O-dimethoxytrityldeoxyribonucleoside units (Annex 2)

3'-O-DMTr-deoxyribonucleoside 5'-O-succinate

Mixture:

1.0 mmol of 3'-O-DMTr-dN 0.8 wool of succinic anhydride (80 mg)

5 0.5 mmol of dimethylaminopyridine (61 mg)

The reaction of succinic anhydride with the 5'-OH group of the deoxyribonucleosides was always carried out in 5 ml of absolute pyridine with DMAP as catalyst at room temperature overnight. After the reaction was complete, the solution was concentrated, and the pyridine was removed by azeotropic distillation with toluene 3 times. The residue was taken up in dichloromethane and washed with 10% strength ice-cold citric acid solution and $H_2O$, and the organic phase was evaporated in vacuo in a rotary evaporator. The crude product was dissolved in about 3 ml of toluene and precipitated in 200 ml of n-hexane.

Loading of the Support

Mixture:

0.8 mmol of 3'-O-DMTr-dN 5'-O-succinate 0.8 mmol of p-nitrophenol (112 mg)

2.0 mmol of dicyclohexylcarbodiimide 3 g of aminopropylated CPG 10-1400

The protected succinylated deoxyribonucleoside was added to a solution of p-nitrophenol in 5 ml of absolute dioxane and 0.2 ml of pyridine, and subsequently DCCI was added as condensing agent. The reaction was complete after 3 hours. The precipitated dicyclohexylurea was filtered off with suction under argon, and the filtrate was directly added to a suspension of the functionalized support material in 15 ml of absolute DMF. 0.8 ml of triethylamine was added, and the mixture was shaken overnight. The loaded support was then filtered off with suction, washed with methanol and ether and dried in a desiccator. To block unreacted amino groups, the loaded support was shaken with a solution of 1 ml of acetic anhydride and 50 mg of dimethylaminopyridine in 15 ml of absolute pyridine at room temperature for 1 hour, subsequently filtered off with suction, washed with methanol and ether and dried.

EXAMPLE 3

Synthesis of oligoribonucleotides with 2'-fluoro-2'-deoxyuridine units and a 3'—3' phosphodiester linkage at the 3' terminus The modified hammerhead ribozyme (Tab. 1) was synthesized on the 0.2 μmol scale using the Gene Assembler Plus DNA synthesizer from Pharmacia. The support material for the synthesis was functionalized with the deoxyadenosine unit attached via the 5'-hydroxyl group; this resulted in an inverted structure at the 3' terminus of the oligonucleotide in the synthesis. Preparation was carried out by the standard protocol for oligoribonucleotide syntheses by the phosphorous ester amide method.

TABLE 1 fN: 2'-fluoro-2-deoxynucleosides
rN: ribonucleosides p53-INV: 5'-r(AAAGA UCUGA UGAGG CCGUU AGGCC GAAAC AGGG)-3'-3'-dA-5' (SEQ ID NO:1)
Fp53-INV: 5'-rArArArGrA fUrCfUrGrA fUrGrArGrG rCrCrGfUfU rArGrGrCrC rGrArArArC rArGrGrG-3'-3'-dA-5'

The phosphorous ester amides of the 2'-fluoro-2'-deoxynucleosides were employed 0.12 M in acetonitrile. In the chain-extension step, 0.1 ml of the amidophosphite is reacted with 0.37 ml of the tetrazole solution (0.5 M) with the support-bound 5'-hydroxyl groups of the oligonucleotide. A coupling time of 12 minutes is followed by standard capping, oxidation and, to prepare for the next coupling steps detritylation. The coupling yields were 99% on average.

To eliminate the base-labile protective groups and to cleave the attachment, the support is transferred after the synthesis into a screw-cap Eppendorf reaction vessel. Incubation was carried out with 2 ml of a 3:1 mixture of 32% strength ammonia and ethanol at 55° C. for 12 hours. The supernatant solution was separated off, cooled to −20° C. and carefully lyophilized. The dry residue was suspended in 0.4 ml of a 1.1 M TBAF solution in THF and incubated at room temperature for a further 16 hours. The reaction was stopped by adding the same volume of a triethylammonium acetate buffer (TEAA buffer). The solution was cooled to −70° C. and cautiously concentrated to 0.4 ml. After addition of 40 μl of sodium acetate, 1.4 ml of ethanol and 5 μl of acetic acid, the product was precipitated at −20° C. overnight. The sample was centrifuged and the supernatant was discarded. The dry oligonucleotide was taken up in a 1:1 mixture of formamide blue marker and water in order to load it onto an acrylamide gel (20%, 7 M urea). In order to identify and cut out the product band, the gel was covered with cellophane films. Elution was carried out with ammonium acetate solution at 40° C. After 5 hours, the solution was precipitated as described above. The oligonucleotide was washed with 70% strength ethanol, resuspended in 70% strength ethanol and stored at −70° C.

EXAMPLE 4

Investigation of the Stability of the Modified Ribozymes in the Blood Serum Test The ribozyme p53 and the modified oligoribonucleotides p53-INV and Fp53-INV were radioactively labeled enzymatically by T4-oligonucleotide kinase in the presence of (γ-$^{32}$P)-dATP (specific activity: 4500 Ci/mmol). The sequences with a 3'—3' inversion have a 5'-hydroxyl group at both ends and are therefore phosphorylated on both ends in some cases.

The labeled ribozymes were treated with fresh human serum.

Mixture:
1 pmol of phosphorylated ribozyme
20 μl of serum

The samples were incubated at 37° C. 2 μl samples were removed and treated with phenol after the following times:

p53: 0, 1, 2, 5, 10, 15, 30, 60 min.
p53-INV and Fp53-INV: 0, 1, 2, 5, 10, 15, 30, 60, 120, 240 min.

The phenol-treated samples were lyophilized, taken up in 95% formamide loading buffer and fractionated by electrophoresis on a 20% polyacrylamide gel with 8 M urea at 55° C.

Figure 1:
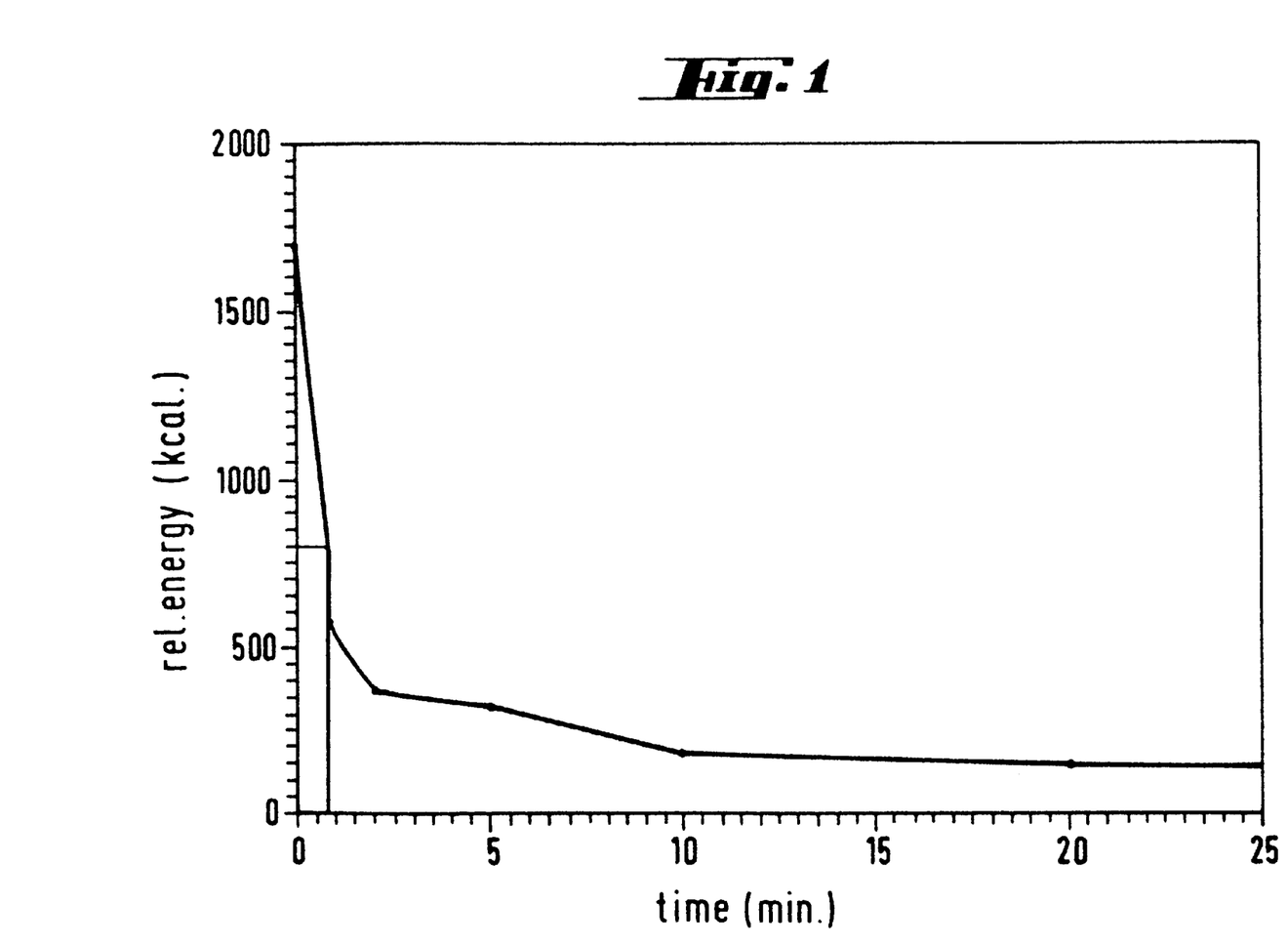
FIG. 1: Stability of p53-INV in serum

The intensity of the bands on the X-ray film was determined with the aid of a laser densitometer (see FIG. 1). The half-lives of the investigated ribozymes (t1/2=30 min for Fp53-INV, 1 min for p53-INV and <<1 min for the biological oligoribonucleotide p53; see Example 5) clearly show the protective effect of the terminal inversion.

EXAMPLE 5

A 20-mer substrate oligoribonucleotide, SB-1(SEQ ID NO:2)5'-r(GC CCC UGU CAU CUU UUG UCC)-3' was radioactively labeled at the 5' end enzymatically using T4 polynucleotide kinase in the presence of $^{32}$P-ATP (specific activity: 4500 Ci/mmol).

The cleavage reaction of SB-1 by various ribozymes was carried out as follows: the reaction conditions were 50 mM tris HCl, pH 7.5, 20 mM MgCl$_2$ at 50° C. The SB-1 substrate concentration was 0.025 μM (varied to 0.05, 0.1 and 0.25 μM), and the ribozyme concentration was 0.02 μM. During the course of 30 min, a sample was taken at 1 min, 5 min, 10 min, 15 min and 30 min and mixed with loading buffer. The samples were fractionated by electrophoresis on a 20% polyacrylamide gel (8 M urea) at 55° C. The decrease in the intensity of the bands of SB-1 was determined on the X-ray film using a laser densitometer.

The following ribozymes were employed:

p53-INV; Fp53-INV (see above in each case); p53 and Pp53 p53(SEQ ID NO:3):5'-r(AAGA UCUG4 UGAGG CCGUU AGGCC GAAAC AGGGA)-3'

Fp53: 5'-r(AAAGA fUCfUGA fUGAGG CCGfUfU AGGCC GAAAC AGGGA)-3'

The rate of cleavage of SB-1 does not differ on use of p53 and p53-INV. Fp53 and Fp53-INV also have the same activity which is, however, a factor of about 5 less than that of p53.

EXAMPLE 6

Substrate Cleavage and Kinetic Measurements

The measurement of the preliminary initial rates of the reaction was carried out with 40 nM substrate and 4 nM enzyme in 50 nM tris-Cl (pH 7.5). The reaction was started by adding 10 nM MgCl$_2$. The amount of the cleavage product was measured after 1, 2, 5, 10 and 15 minutes at 55° C. The R value was determined approximately from this experiment. More accurate measurements of the initial reaction rates were carried out as described by Suelter, C. H. (1985) in "A practical Guide to Enzymology", J. Wiley New York, 231. This entailed six separate reactions being carried out with 40 nM enzyme and 25 nM, 50 nM, 100 nM, 200 nM, 500 nM and 1000 nM substrate respectively. A 2 μl aliquot was removed after defined time intervals, and the reaction was stopped by addition of phenol. The samples were then fractionated and analyzed on a denaturing gel (20% PAGE, 7 M urea).

| | |
|---|---|
| Substrate: | SB-1 (Example 5) |
| Ribozymes: | p53-INV (Example 3) |
| | p53-F(U,C),INV: 5'-rArArArGrA fUfCfUrG |
| | rAfUrGrArGrGfCfCrGfUfUrArGrGfC |
| | fCrGrArArAfCrArGrGrG-3'-3'-dA-5' |
| | p53-1(SEQ ID NO:4): 5'-r (AAA GAU CUG AUG AGG |
| | CCG UUA GGC CGA AAC AGG G)-3' |

Determination of the kinetic parameters

Figure 2:
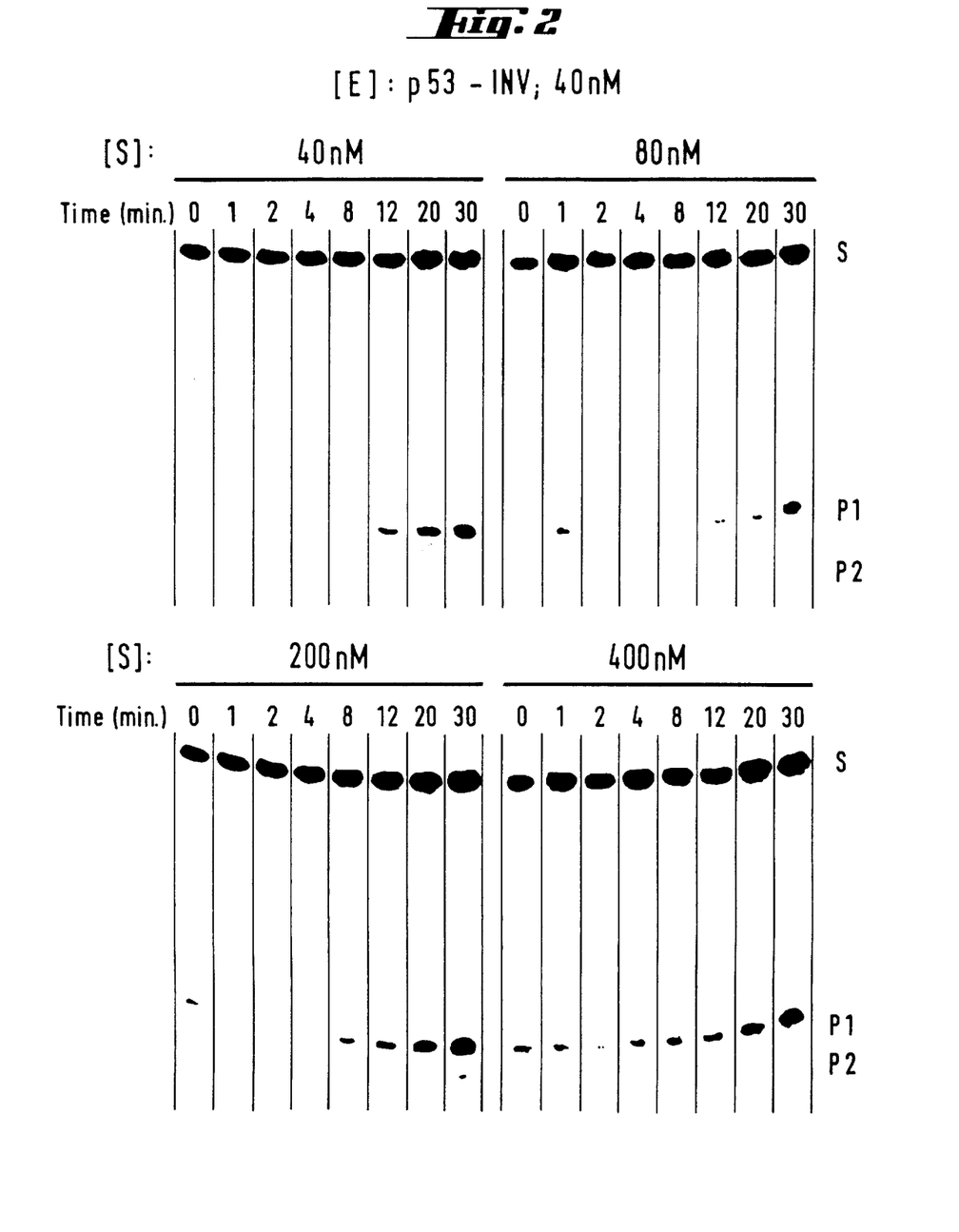
FIG. 2: Kinetics of substrate cleavage by modified ribozymes

The initial reaction rate was determined at 5 different substrate concentrations for the early phase of the progression curve at the time at which the rate of product formation was linear (after 4 minutes). Typical results of these kinetic measurements are shown in FIG. 2. Since in our experiments the reactions were started by adding doubly charged cations to the reaction mixture, and the formation of the enzyme conformation was thus not allowed, a lag phase was usually observed 5 to 10 minutes after the start of the reaction.

The following enzymatic parameters were determined from an Eadie-Hofstee plot.

TABLE 2

| Ribozyme | $K_m$ (nM) | $V_{max}$ (min$^{-1}$) | $K_{cat}$ (min$^{-1}$) | $K_{cat}/K_m$ ($\mu M^{-1}$ min$^{-1}$) |
|---|---|---|---|---|
| p53-1 | 24 | 8.6 | 0.21 | 8.75 |
| p53-INV | 230 | 52.3 | 1.30 | 5.65 |
| p53-F(U,C),INV | 180 | 40.9 | 1.02 | 5.56 |

EXAMPLE 7

Labeling

Substrate and enzymes were radioactively labeled with [γ-$^{32}$P]ATP and polynucleotide kinase. Non-incorporated nucleotides were removed by phenol extraction with subsequent ethanol precipitation.

Test to Determine Degradation

The kinetics of the degradation with modified ribozymes was determined by dissolving the radioactively labeled oligoribonucleotides in pooled, fresh and non-diluted human serum at a final concentration of 20,000 cpm/μl. After an initial sample had been taken, the reaction mixture was incubated at 37° C. 1 μl aliquots were removed after defined time intervals and the reaction was stopped with phenol. After the phenol extraction and ethanol precipitation, the samples were suspended in 80% formamide which contained 20 nM EDTA, 0.01% bromophenol blue and 0.01% of xylene cyanole. The cleavage products were fractionated on a 20% polyacrylamide gel (PAGE) with 7 M urea.

Figure 3:
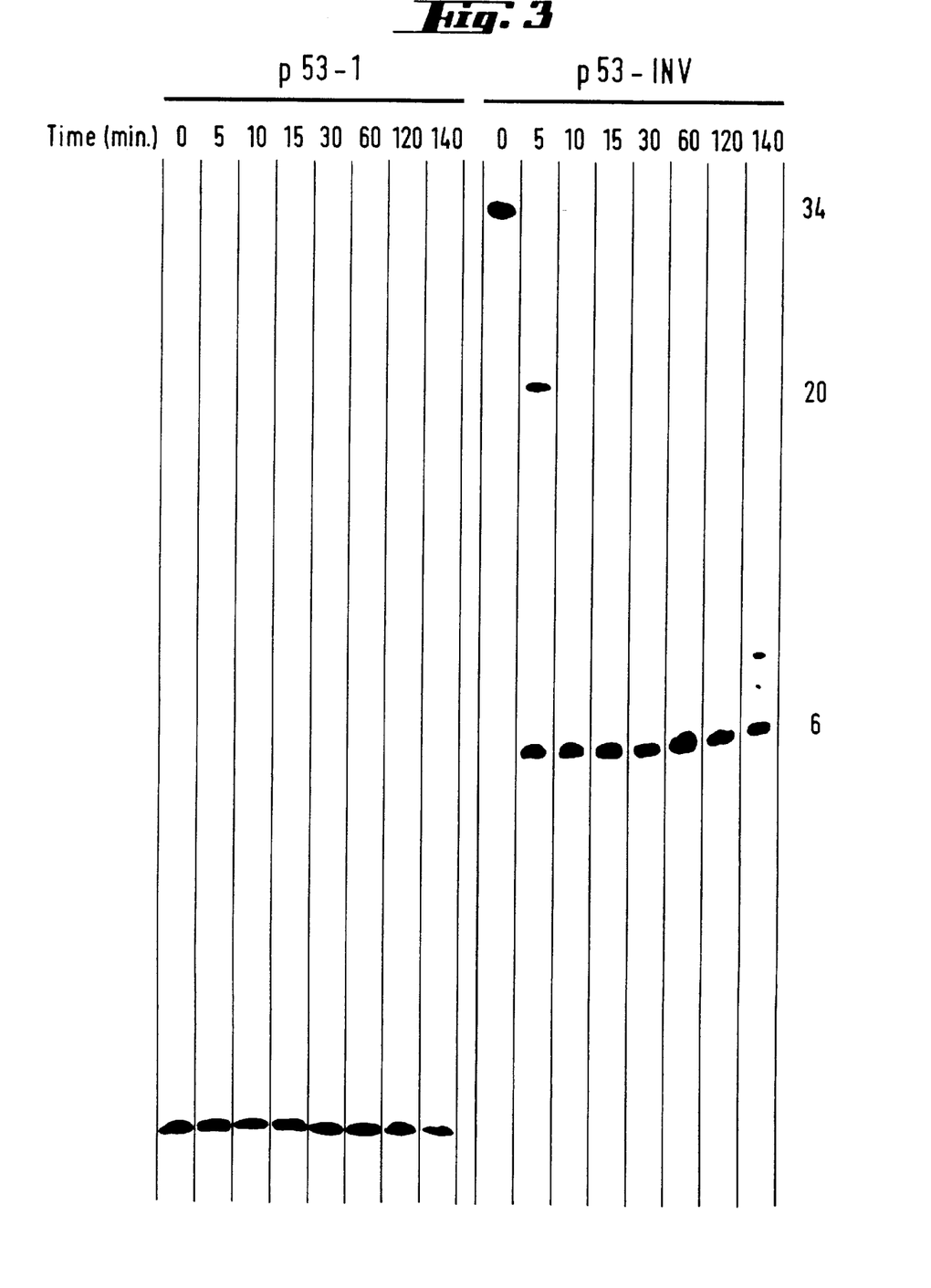
FIG. 3: Nucleolytic degradation of p53-1 and p53-INV

The results of the incubation of p53-1 and p53-INV are shown in FIG. 3. It is evident from the figure that an inverted structure at the 3' terminus by itself brings about an improvement in the stability of the ribozymes in the presence of serum, from less than 10 seconds to up to several minutes.

The experiments were carried out with 1 pmol of unmodified (p53-1) and modified (p53-INV) ribozymes in 10 μl of undiluted human serum at 37° C. The numbers on the edge of the gel correspond to the positions of appropriate length standards.

Figure 4:
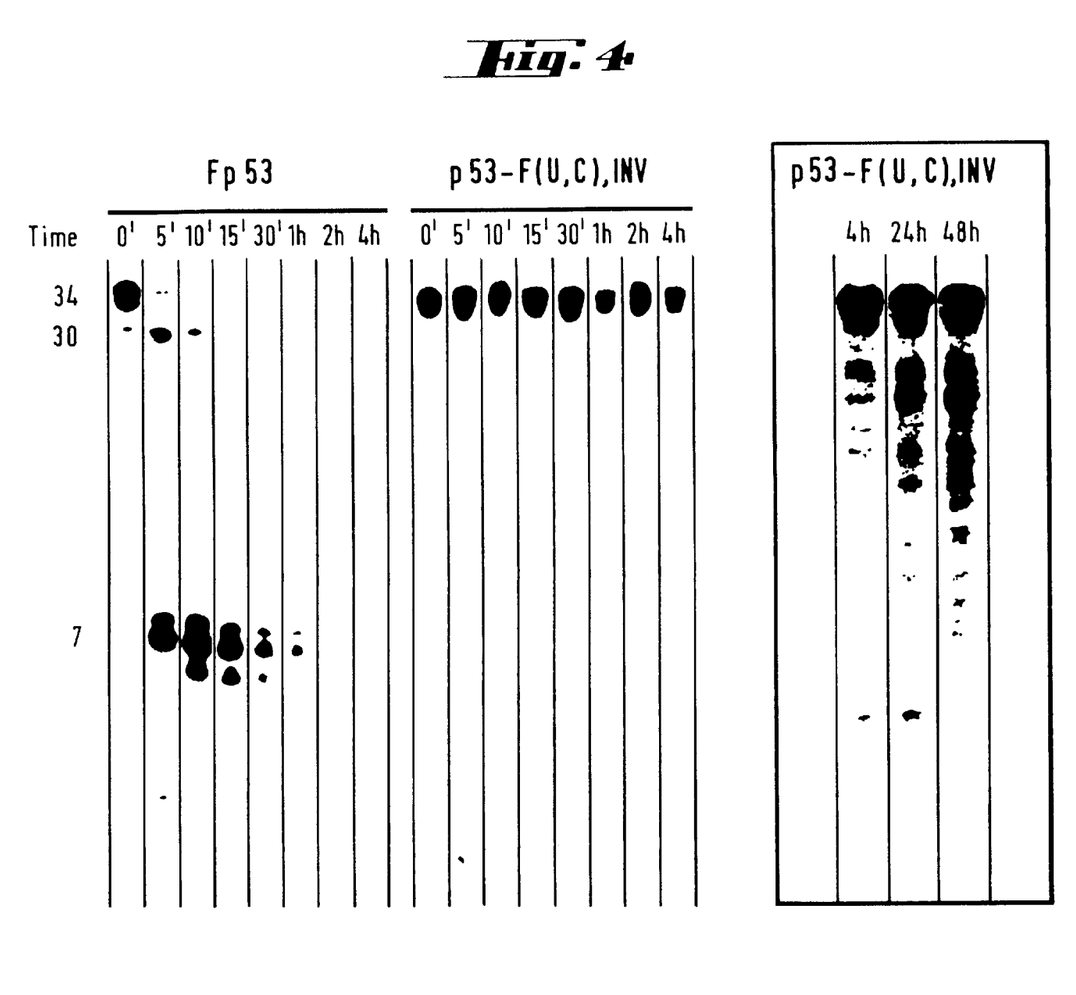
FIG. 4: Nucleolytic degradation of Fp53-INV and p53-F(U,C),INV

The results of the incubation of Fp53 and p53-F(U,C), INV are shown in FIG. 4. It is evident from this that no degradation was observed with p53-F(U,C),INV after incubation in undiluted serum for 4 hours. Less than 10% degradation was observed after 48 hours. The experiments were carried out with 1 pmol of modified ribozymes, where Fp53 has an inverted structure at the 3' terminus and is fluorinated at positions $U_6$, $U_8$, $U_{11}$, $U_{19}$ and $U_{20}$. p53-F(U, C),INV is additionally fluorinated on the cytosine residues $C_7$ and $C_{30}$.

Annex 1

Synthesis of $_2$1-fluoro-2'-deoxycytidine-(A) and 2'-fluoro-2'-deoxyuridine-phosphorous aster amide (B)

Annex 2

Synthesis of 3'-O-DMTr-deoxyribonucleoside 5'-O-succinyl-p-netrophenyl ester and loading of the controlled pore glass support material

6. phosphitylation
(1)/EtN$^i$Pr$_2$ (1):

-continued

B = thymine
 N⁵ - benzoyladenine
 N⁴ - benzoylcytosine
 N² - isobutyrylguanine
DMTr = 4,4' - dimethoxytrityle

What is claimed is:

1. An oligoribonucleotide of the formula I in which $R^1$ is hydrogen or a radical of the formula II $R^2$ is hydrogen or a radical of the formula III but where at least one of the radicals $R^1$ or $R^2$ is a radical of the formula II or III;

B is a base such as, for example, natural bases such as adenine, thymine, cytosine, guanine or unnatural bases such as, for example, purine, 2,6-diaminopurine, 7-deazaadenine, 7-deazaguanine, $N^4,N^4$-ethanocytosine or their prodrug forms;

$R^3$ is, independently of one another, OH, hydrogen, $O(C_1-C_{18})$alkyl, $O(C_2-C_{18})$alkenyl, F, $NH_2$ or its prodrug forms and $N_3$, but at least one $R^3$ radical is different from H, and $R^3$ is preferably OH, hydrogen, $O(C_1-C_6)$alkyl, $O(C_2-C_6)$alkenyl, F, $NH_2$ and very preferably OH;

W and W' are, independently of one another, oxygen or sulfur;

Z and Z' are, independently of one another, $O^-$; $S^-$; $C_1-C_{18}$-alkoxy, preferably $C_1-C_8$-alkoxy, particularly preferably $C_1-C_3$-alkoxy, especially methoxy; $C_1-C_{18}$-alkyl, preferably $C_1-C_8$-alkyl, particularly preferably $C_1-C_3$-alkyl, especially methyl; $NHR^4$, with $R^4$=preferably $C_1-C_{18}$-alkyl, particularly preferably $C_1-C_8$-alkyl, especially $C_1-C_4$-alkyl or $C_1-C_4$-alkoxy-$C_1-C_6$-alkyl, preferably methoxyethyl; $NR^4R^5$, in which $R^4$ is as defined above and $R^5$ is preferably $C_1$–$C_{18}$-alkyl, particularly preferably $C_1$–$C_8$-alkyl, especially $C_1$–$C_4$-alkyl, or in which $R^4$ and $R^5$ are, together with the nitrogen atom carrying them, a 5–6-membered heterocyclic ring which may additionally contain another hetero atom from the series comprising O, S and N, such as, for example, morpholine;

where X is OH, H, F, Cl, Br, $NH_2$, $N_3$, O—C(O)—($C_1$–$C_{18}$)-alkyl, O—C(O)—($C_2$–$C_{18}$)-alkenyl, O—C(O)—($C_2$–$C_{18}$)alkynyl, O—C(O)—($C_6$–$C_{18}$) aryl, O—($C_1$–$C_{18}$)-alkyl, O—($C_2$–$C_{18}$)-alkenyl, O—($C_2$–$C_{18}$)alkynyl, O—($C_1$–$C_{18}$)aryl, P(O)YY', where Y and Y' are defined as Z and Z'. $R^3$ and X in formula II can together form a cyclic phosphoric diester;

X is preferably OH, H, F, particularly preferably OH;

n is an integer from 5–60, preferably 10–40 and especially preferably 15–25, and its physiologically tolerated salts.

2. An oligoribonucleotide of the formula I as claimed in claim 1, wherein $R^2$ is a radical of the formula III and $R^{1'}$ is hydrogen; $R^1$ and $R^2$ are a radical of the formulae II and III respectively; or $R^2$ is hydrogen and $R^1$ is a radical of the formula II, where either W or Z in the latter case is not oxygen, and X is OH or H.

3. An oligoribonucleotide of the formula I as claimed in claim 1, wherein $R^2$ is a radical of the formula III and $R^1$ is hydrogen.

4. An oligoribonucleotide of the formula I as claimed in claim 1, wherein it is additionally substituted by groups which favor intracellular uptake, which act in vitro or in vivo as reporter groups, and/or groups which, on hybridization of the oligonucleotide onto biological DNA or RNA, interact with these DNA or RNA molecules with binding or cleavage.

5. A process for the preparation of the oligoribonucleotides of the formula I as claimed in claim 1, which comprises a) reacting a nucleotide unit with 3'- or 5'-terminal phosphorus(III) or phosphorus(V) groups or its activated derivative with another nucleotide unit with a 3'- or 5'-terminal free hydroxyl group, or b) assembling the oligonucleotide by fragments in the same way, eliminating where appropriate one or more protective groups temporarily introduced to protect other functionalities in the loigonucleotides obtained according to a) or b). and converting the oligonucleotides of the formula I obtained in this way where appropriate into their physiologically tolerated salt.

6. A pharmaceutical containing one or more of the compounds as claimed in claim 1, where appropriate together with physiologically tolerated ancillary substances and/or vehicles, preferably for intravenous or topical administration.

7. An oligoribonucleotide of the formula I in which
$R^1$ is H or a radical of the formula II $R^2$ is a radical of the formula III B is adenine, thymine, cytosine, guanine, purine, 2,6-diaminopurine, 7-deazaadenine, 7-deazaguanine, or $N^4$, $N^4$-ethanocytosine;

$R^3$ is, independently of one another, OH, H, or F, and wherein at most one R3 radical is H;

W and W' are, independently of one another, oxygen or sulfur;

X is OH, H, or F;

Z and Z' are, independently of one another, $O^-$ or $S^-$;

where n is an integer from 5–60;

or its physiologically tolerated salt, except the oligoribonucleotide wherein $R^3$ is F and B is a purine.

8. An oligonucleotides of the formula I as claimed in claim 7 wherein W is oxygen, or Z and W are both oxygen.

9. A ribozyme of the formula I as claimed in claim 7.

10. A method of preparing oligonucleotides for the regulation or suppression or the biological function of nucleic acids comprising the step of using the ribonucleotide as claimed in claim 7 in chemical hybridization methods which involve adding to double- or single-stranded nucleic acids.

* * * * *

UNITED STATES PATENT AND TRADEMARK OFFICE
CERTIFICATE OF CORRECTION

PATENT NO. : 6,420,546 B1
DATED : July 16, 2002
INVENTOR(S) : Seliger et al.

It is certified that error appears in the above-identified patent and that said Letters Patent is hereby corrected as shown below:

Column 21,
Line 41, "O-($C_1$-$C_{18}$)aryl" should read -- O-($C_6$-$C_{18}$)aryl --.
Line 24, "$R^{1,}$" should read -- $R^1$ --.
Line 53, "loigonucleotides" should read -- oligonucleotides --.
Line 54, "b)." should read -- b), --.

Column 22,
Line 47, "R3" should read -- $R^3$ --.
Line 54, "oligonucleotides" should read -- oligonucleotide --.

Signed and Sealed this

Fourth Day of January, 2003

JAMES E. ROGAN
*Director of the United States Patent and Trademark Office*